United States Patent [19]

Eguchi et al.

[11] Patent Number: 4,719,200
[45] Date of Patent: Jan. 12, 1988

[54] AMINO ACID DERIVATIVES AND ANTIHYPERTENSIVE DRUGS CONTAINING THE SAME

[75] Inventors: Chikahiko Eguchi, Yokohama; Masahiko Kurauchi, Nagashino; Shumpei Sakakibara, Suita, all of Japan

[73] Assignee: Ajinomoto Co., Inc., Tokyo, Japan

[21] Appl. No.: 769,029

[22] Filed: Aug. 26, 1985

[30] Foreign Application Priority Data

Aug. 24, 1984 [JP] Japan .................. 59-176355

[51] Int. Cl.$^4$ .................. A61K 37/02; C07K 5/08; C07K 5/10
[52] U.S. Cl. .................. 514/18; 530/330; 530/331
[58] Field of Search .................. 530/331, 330; 514/18

[56] References Cited

FOREIGN PATENT DOCUMENTS 0085488 8/1983 European Pat. Off. .
2621279 11/1977 Fed. Rep. of Germany .

OTHER PUBLICATIONS

Synthetic Peptides, vol. 6 (1984), pp. 224, 225, 240, 241 & 266.
Synthetic Peptides, vol. 5 (1980), pp. 148, 149, 176, 177, 184, 185, 186, 187, 192, 193.
Synthetic Peptides, vol. 3 (1978), pp. 196 & 197.
Synthetic Peptides, vol. 1 (1971), 224 & 225.
Chem. Abstr., vol. 104 (1986), 110180.

*Primary Examiner*—Delbert R. Phillips
*Attorney, Agent, or Firm*—Oblon, Fisher, Spivak, McClelland, & Maier

[57] ABSTRACT

An amino acid derivative having anti-hypertensive activity and having the formula:

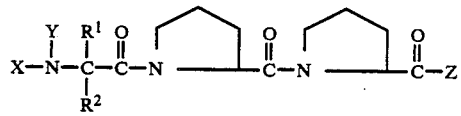

wherein one of X or Y represents an acyl group RCO—, and wherein R is an amino acid residue selected from the group consisting of glycyl, alanyl, valyl, leucyl, isoleucyl, phenylalanyl, methionyl, prolyl, ceryl, threonyl, arginyl, lysyl, histidyl, aspartyl, asparaginyl, tyrosyl, cysteinyl, tryptophyl, and hydroxyprolyl, and the other group is H; $R^1$ and $R^2$ are the same or different from each other, and each represents H, lower alkyl having 1 to 6 carbon atoms, aryl having 6 to 12 carbon atoms, any of which are unsubstituted or substituted by one or more lower alkyl, lower alkoxy, hydroxy, amino, carboxy or mercapto groups; Z represents —OH, RO—, RS—, RNH—, NONH—, RONH—, RSO$_2$NH—, RCONH—, or RCSNH—; and wherein R as defined above for the moiety Z is H, lower alkyl having 1 to 6 carbon atoms, aryl having 6 to 12 carbon atoms or aralkyl having 6 to 12 carbon atoms, any of which are unsubstituted or substituted by one or more lower alkyl, lower alkoxy, hydroxy, amino, carboxy or mercapto groups.

11 Claims, No Drawings

AMINO ACID DERIVATIVES AND ANTIHYPERTENSIVE DRUGS CONTAINING THE SAME

BACKGROUND OF THE INVENTION

1. Field of the Invention

The present invention relates to amino acid derivatives and antihypertensive drugs containing the same.

2. Description of the Background

Several classes of antihypertensive compounds are known. However, many are difficult to synthesize or have relatively low antihypertensive activities. Thus, a need continues to exist for antihypertensive compounds which are relatively easy to synthesize and which have an excellent antihypertensive activity.

SUMMARY OF THE INVENTION

Accordingly, it is an object of the present invention to provide compounds having an excellent antihypertensive activity.

It is also an object of this invention to provide antihypertensive compounds which are relatively easy to snythesize.

Further, it is also an object of the present invention to provide an antihypertensive composition containing the above compounds.

Moreover, it is also an object of this invention to provide a method for treating hypertension in mammals.

According to the present invention, the foregoing and other objects are attained by providing an amino acid derivative having the formula:

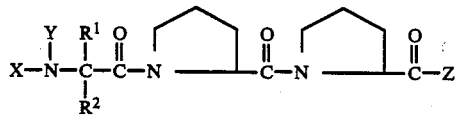

wherein X represents a hydrogen atom, R— or RCO—; Y represents hydrogen atom, R—, RCO—, RCS—, $RSO_2$— $ROSO_2$—, ROCO—, RSCO—, ROCS—, RSCS—, RHNCO—, RR'NCO—, RNHCS—, RR'NCS—, RC(NR')—, $RC(NNH_2)$—, RC(NNOH)—, RNH—, RR'N—, RO—, NC—, $RNHSO_2$, OR $O_2N$—; $R^1$ and $R^2$ are the same or different from each other, and each represents H, lower alkyl having 1 to 6 carbon atoms, aryl having 6 to 12 carbon atoms, any of which are unsubstituted or substituted by one or more lower alkyl, lower alkoxy, hydroxy, amino, carboxy or mercapto groups; and Z represents —OH, RO—, RS—, RNH—, HONH—, RONH—, $RSO_2NH$—, RCONH—, OR RCSNH—, and wherein R or R' in the above formulas represents alkyl, aryl or aralkyl groups which are unsubstituted or substituted by one or more lower alkyl, lower alkoxy, hydroxy, amino, carboxy or mercapto groups, X and Y are the same or different from each other or are combined together to form a bridge having 1 to 12 carbon atoms or 1 to 12 carbon atoms containing one or more heteroatoms such as O, N or S, said bridge being unsubstituted or substituted by lower alkyl, lower alkoxy, hydroxy, amino, carboxy or mercapto groups, and in the acyl group RCO—, R, in addition to being defined as above, also may be an amino acid residue; with the exclusion of the compounds where Y is t-butyloxycarbonyl or benzyloxycarbonyl, where Y is t-amyloxycarbonyl and $R^2$ is H and X and $R^1$ are combined together to form a propylene bridge and Z is hydroxy or benzyloxy, where Y is isobutyloxy and X and $R^2$ are H and $R^1$ is sec-butyl and Z is benzyloxy, where Y is triphenylmethyl and X and $R^1$ and $R^2$ are H and Z is hydroxy, where Y is O-nitrophenyl sulfenyl and $R^2$ is H and X and $R^1$ are combined together to form a propylene bridge and Z is hydroxy or 2,4,5-trichlorophenyloxy, where Y is palmitoyl or lauroyl or 2,2-dimethyl butanoyl or isonicotinoyl and $R^2$ is H and X and $R^1$ are combined together to form a propylene bridge and Z is hydroxy, where Y is acetyl and X and $R^2$ are H and $R^1$ is 1-hydroxyethyl and Z is hydroxy, where Y is trifluoroacetyl and X and $R^2$ are H and $R^1$ is isobutyl and Z is methoxy, and where Y is isobutyl and Z is methoxy, and where Y is 6-chloro-2-methoxy-9-acridinyl and X and $R_1$ and $R_2$ are H and Z is hydroxy.

DETAILED DESCRIPTION OF THE PREFERRED EMBODIMENTS

According to the present invention, amino acid derivatives of the tripeptide alanyl-prolyl-proline are provided having the formula:

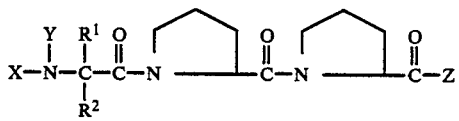

These compounds exhibit excellent antihypertensive activity and the synthesis thereof is relatively easy.

In the above general formula, X represents a hydrogen atom, R— or RCO—; Y represents a hydrogen atom, R— or RCO—, RCS—, $RSO_2$, $ROSO_2$—, ROCO—, RSCO—, ROCS—, RSCS—, RNHCO—, RR'NCO—, RNHCS—, RR'NCS—, RC(NR')—, $RC(NNH_2)$—, RC(NNOH)—, RNH—, RR'N—, RO—, RS—, NC—, $RNHSO_2$—, or $O_2N$—; $R^1$ and $R^2$ are the same or different from each other, and each represents H, lower alkyl having 1 to 6 carbon atoms, aryl having 6 to 12 carbon atoms, any of which are unsubstituted or substituted by one or more lower alkyl, lower alkoxy, hydroxy, amino, carboxy or mercapto groups; and Z represents —OH, RO—, RS—, RNH—, HONH—, RONH—, $RSO_2NH$—, RCONH—, or RCSNH—.

R and R' of X, Y and Z in the foregoing formula, each individually represents a lower alkyl or cycloalkyl group having 1 to 6 carbon atoms which may or may not have any substituents such as methyl, ethyl, n-propyl, n-butyl, t-butyl, cyclopentyl, cyclohexyl, carboxymethyl, carboxyethyl, aminomethyl, aminoethyl, hydroxymethyl, hydroxyethyl, mercaptomethyl and mercaptoethyl group, an aryl group having 6 to 12 carbon atoms which may or may not have any substituents such as phenyl, naphthyl, p-tolyl, biphenyl, aminophenyl, hydroxy, hydroxyphenyl, and mercaptophenyl group, an aralkyl group having 6 to 12 carbon atoms which may or may not have any substituents such as benzyl, phenethyl, phenylpropyl, aminobenzyl, hydroxybenzyl, and mercaptobenzyl groups, and an alkyl group, an aryl group or aralkyl group which may involve a hetero ring having 1 to 12 carbon atoms which may or may not have any substituents such as furyl, thienyl, pyrrolyl, pyridyl, guinolyl, thiazolyl, imidazolyl, indolyl, carbazolyl, purinyl, furfuryl, thenyl, pyridylmethyl, indolyl, pyrrodinyl, and piperidinyl group.

R and R' of X, Y and Z may also be combined together to form a bridge, R-R', with the bridge being an alkane diyl group having 1 to 12 carbon atoms which is unsubstituted or substituted and can be groups such as methylene, ethylene, propane diyl, butane diyl, pentane diyl, and cyclohexane diyl group; or the bridge may be an arene diyl having 1 to 12 carbon atoms which may or may not have any substitutents such as phenylene, naphthalene, naphthalene diyl, furan diyl, pyridine diyl, imidazolyl diyl, and indole diyl group. All of these bridges can be substituted by lower alkyl, lower alkoxy, hydroxy, amino, carboxy or mercapto groups The bridges can also contain one or more of the heteroatoms O, N or S.

X or Y may represent, among other things, an acyl group of the formula RCO—, wherein R of this group also may represent an amino acid residue such as glycyl, alanyl, valyl, leucyl, isoleucyl, phenylalanyl, methionyl, prolyl, seryl, threonyl, arginyl, lysyl, histidyl, glutamyl, aspartyl, glutaminyl, asparaginyl, tyrosyl, cysteinyl, tryptophyl, pyroglutamyl, and hydroxyprolyl group.

As is clear from the above descriptions, it is characteristic that the amino acid derivatives of the present invention show an excellent antihypertensive activity however diversely they are substituted The amino acids of the amino acid derivative of the present invention may be either the L-isomer or the D-isomer.

The amino acid derivatives of the present invention may be in the form of a salt, such as a metal salt, as for example, a sodium, potassium, lithium, or calcium salt, or a salt with an organic base. As the organic base, there can be used amines such as ammonia (ammonium salt), dicyclohexyl amine, and N-methyl-D-glucamine; or basic amino acids such as lysine and arginine.

When the amino acid derivatives are to be included in the antihypertensive drugs of the present invention, they, of course, must be in a form of a pharmaceutically acceptable salt.

The amino acid derivatives of the present invention can be prepared, for example, by reacting an alanine having a protected amino group therein with a proline having a protected carboxyl group therein to prepare alanyl-proline, removing the protecting group from the carboxyl group therein, and then reacting the resulting product with a proline moiety having a protected carboxyl group therein, and followed, if necessary, by removing the protecting group, to thereby synthesize a tripeptide of alanyl-prolyl-proline, and then replacing a hydrogen atom in the terminal amino group thereof with a functional group such as an acyl group.

The protecting groups for amino, imino, carboxyl, and hydroxyl groups, as well as the methods for their protection, the methods for removal of the protecting groups, and the methods for amino-linking by condensation between amino and carboxyl groups, which are employed in the preparation of the derivatives of the present invention, and the intermediates therefor may be the ones ordinarily used in the methods for peptide synthesis or those generally or conventionally employed in the known literature, for example, Protein Chemistry, 1 Amino Acid, Peptide, e.g., pages 405–509 (1969), compiled by Shiroh Akabori, Takeo Kaneko, and Kozo Narita, published by Kyoritsu Shuppan Co. Further, an amide-linkage can be advantageously formed from an amino acid by condensation in which an active ester of the amino acid having a protected amino group, such as p-nitrophenylester and N-hydroxysuccinimidester is used for reaction When a solvent is used in the reaction, dimethylformamide (abbreviated as DMF) or water can be adopted as a solvent. The reaction temperature may be approximately room temperature but the reaction can also, as needed, be accelerated by heating.

The derivatives of the present invention are isolated from the reaction mixture by concentrating the reaction mixture to dryness, purifying the residue by means of column chromatography followed by lyophilization of the product.

When the derivatives of the present invention are used, as an active ingredient for an antihypertensive drug, there may be used their free forms, their nontoxic forms as salts, or their forms having protecting groups. The non-toxic amino acids constituting the derivatives for use as an antihypertensive drug of the present invention may be either the L-isomer or the D-isomer The amino acid derivatives of the present invention are useful as an antihypertensive drug for treating hypertensive mammals including humans. The derivatives can be used for lowering blood pressure by formulating them into preparations such as tablets, capsules, and elixirs for oral administration and into aseptic liquid preparations such as an aseptic suspension for parenteral administration. However, the amino acid derivatives of the present invention can be administered in any manner, including by injection. The amino acid derivatives of the present invention can be administered to a subject in need of such treatment, i.e., animals or humans, in a dosage range of about 0.2 to 500 mg per subject generally several times a day, that is, in a total daily dosage of about 1 to 2000 mg. The dosage varies according to the seriousness of disease, the body weight of the subjects, and other factors acknowledged by those skilled in the art.

The amino acid derivatives of the present invention can also be administered together with diuretics or other antihypertensive drugs. Typically, these drugs are administered in a dosage combination of which one unit of daily dose is in the range from $\frac{1}{5}$ times as large as a clinical dosage minimally recomnended, to a level maximally recommended singly for each entity of disease. For example, the particular antihypertensive drugs of the present invention which might be clinically effective in a daily dosage range of 15 to 200 mg can effectively be administered together which the following other antihypertensive drugs and diuretics in a daily dosage range of 3 to 200 mg: hydrochlorothiazide (15 to 200 mg), chlorothiazide (125 to 2000 mg), ethacrynic acid (15 to 200 mg), amiloride (5 to 20 mg), furosemide (5 to 80 mg), propranolol(20 to 480 mg), timolol (5 to 50 mg) and methyldopa (65 to 2000 mg). The foregoing dosage ranges are adjusted on the basis of unit according to the need within the range of possible daily divided dosage The dosage varies according to the seriousness of disease, the body weight of subject, and other factors acknowledged by those skilled in the art.

The foregoing typical combinations of drugs are formulated into the pharmaceutical compositions stated below. About 0.2 to 500 mg of the derivatives of the present invention, their pharmaceutically acceptable salt compounds, or mixtures of both are blended into unit dosage forms generally acknowledged or required for the pharmaceutical practice together with pharmaceutically acceptable vehicles, carriers, excipients, binders, antiseptics, stabilizers, flavorings, and so forth. The amount of each active substance in these compositions or preparations is adjusted in such a way as to give an appropriate dosage of the prescribed range.

Specific materials which can be incorporated into tablets, capsules, and so forth are as follows: a binder such as tragacanth, gum arabic, cornstarch, and gelatin; an excipient such as microcrystalline cellulose; a swelling agent such as cornstarch, pregelatinized starch, and arginic acid, a lubricant such as magnesium stearate; a sweetener such as sucrose, lactose, and saccharin; a flavoring such as peppermint, an oil from Gaultheria adenothrix Maxim, and cherry. When the unit dosage form of the preparation is a capsule, a liquid carrier such as fatty oil can further be incorporated in the foregoing type materials. Various other materials can be present as a coating material or in order to vary the physical form of unit dosage form according to other methods. For example, tablets can be coated with shellac and/or sugar. Syrups or elixirs can contain active compounds, sucrose as a sweetener, methyl- and propylparaben as an antiseptic, a coloring matter, a flavoring such as cherry and an organic flavoring.

Aseptic compositions for injection can be formulated according to the usual practice for preparation of pharmaceutical dosage forms, in which practice an active substance is dissolved or suspended in a vehicle such as water for injection; natural vegetable oils such as sesame oil, palm oil, peanut oil, and cotton seed oil; and synthetic fat vehicle such as ethyl oleate. A buffer, an antiseptic, and antioxidant can further be incorporated as occasion demands.

The present invention will be further illustrated by certain examples and references which are provided for purposes of illustration only and are not intended to limit the present invention.

EXAMPLE 1

Synthesis of
N-ethoxycarbonyl-L-alanyl-L-prolyl-L-proline

Water (10 ml) and acetone (30 ml) were added to L-alanyl-L-prolyl-L-proline (5.68 g, 20 m mole) and the thus obtained aqueous solution was adjusted to pH 12.0 with 5N aqueous sodium hydroxide. A solution of 90% chloroformic acid ethyl ester (2.92 g, 20 m mole) in 1,2-dichloroethane (5 ml) and 5N aqueous sodium hydroxide were added dropwise at the same time over 30 minutes to the above solution while stirring under a condition of internal temperature below 10° C. and a value of pH 12 to about 12.5. After the completion of the above addition, the thus obtained solution was stirred for 1 hour at the same temperature, and then 1,2-dichloroethane (20 ml) and water (20 ml) were added thereto to make separate phases of water phase and 1,2-dichloroethane phase. To the water solution, 6N hydrochloric acid was added to adjust the pH value to 3.0, and then sodium chloride cyrstals were added thereto to change the solution to a white turbidity. The obtained mixture was extracted with three 30 ml portions of chloroform. The chloroform solution was dried over anhydrous sodium sulfate, and then the chloroform was removed from such solution by distillation under reduced pressure. To the thus concentrated residue, carbon tetrachloride (30 ml) was added, and the solution was concentrated under reduced pressure. Ethyl ether (100 ml) was added to the thus obtained residue, and solidified slowly while stirring. Solid materials were obtained on the paper filter and dried to obtain N-ethoxycarbonyl-L-alanyl-L-prolyl-L-proline (5.7 g).

NMR spectrum [CDCl$_3$, Internal standard TMS]:
1.07~1.45 ppm (m, 6H), 1.63~2.40 ppm (m, 8H),
3.20~3.81 ppm (m, 4H), 4.00 ppm (q, 2H),
4.17~4.68 ppm (m, 3H), 5.45 ppm (d, 1H),
9.00 ppm (s, 1H).

TLC [Ethyl acetate:Methanol =1:1; Iodine] Rf=0.32.

Mass spectrum [FAB mode] M+H=356.

EXAMPLE 2

Synthesis of
N-(3-phenylpropionyl)-L-alanyl-L-prolyl-L-proline
L-arginine salt (a) N-(3-phenylpropionyl)-L-alanyl-L-prolyl-L-proline Phenylpropionic acid (3 g, 20 m mole) was dissolved in 1,2-dichloroethane (80 ml), and while maintaining the solution at an internal temperature between 5 and 8° C., L-alanyl-L-prolyl-L-proline methyl ester hydrochloride (6.69g), triethyl amine (2.02 g, 20 m mole), 1-hydroxybenzotriazole (0.35 g, 3 m mole), and dicyclohexylcarbod iimide (4.12 g, 20 m mole) were added, and the thus obtained mixture was stirred for 4 hours. After that, it was stirred at room temperature overnight, and the precipitated dicyclohexyl urea crystals and triethyl amine hydrochloride crystals were filtered off and were washed with 1,2-dichloroethane (20 ml). The filtrate and the washing were mixed together, and the obtained mixture was washed with 0.5N hydrochloric acid (50 ml), water (80 ml), 0.5N aqueous sodium hydroxide (60 ml) and water (80 ml) in order, and the 1,2-dichloroethane phase was concentrated under reduced pressure To the obtained syrupy residue, water (50 ml) and 5N aqueous sodium hydroxide (5 ml) were added and the obtained mixture was stirred at room temperature for 2 hours. After completion of the saponification, the precipitated dicyclohexyl urea crystals were filtered off and washed with water (5 ml). The filtrate and the washings were mixed together, and the thus obtained mixture was adjusted to pH 2.5 with 6N hydrochloric acid and was extracted with 1,2-dichloroethane (100 ml). The 1,2-dichloroethane phase was washed with water (30 ml), and the 1,2-dichloroethane was distilled off therefrom under reduced pressure To the concentrated residue, carbon tetrachloride (30 ml) was added, and the obtained solution was concentrated under reduced pressure and ethyl ether (100 ml) was added thereto. The solution was changed slowly to a solid material while stirring. A solid material was obtained by filtration, and dried to obtain N-(3-phenylpropionyl)-L-alanyl-L-prolyl-L-proline (5.8 g).

NMR spectrum [CDCl$_3$, Internal standard: TMS]:
1.27 ppm (d, 3H), 1.72~2.31 ppm (m, 8H), 2.32~2.62 ppm (m, 2H), 2.70~3.02 ppm (m, 2H), 3.27~3.88 ppm (m, 4H), 4.32~4.75 ppm (m, 3H), 6.52 ppm (d, 1H), 7.05 ppm (s,5H), 8.99 ppm (s, 1H).

TLC [Ethyl acetate:Methanol=1:1; Iodine] Rf=0.30

Mass spectrum [FAB mode] M+H=416.

(b) N-(3-phenylpropionyl)-L-alanyl-L-prolyl-L-proline-L-arginine salt

N-(3-phenylpropionyl)-L-alanyl-L-prolyl-L-proline (1.00 g, 2.41 m mole) was dissolved in a solution of L-arginine (0.42 g, 2.41 m mole) in water (30 ml), and the thus obtained solution was freeze-dried to give N-(3-phenylpropinyl)-L-alanyl-L-prolyl-L-proline L-arginine salt (1.40 g).

EXAMPLE 3

Synthesis of N-acetyl-L-alanyl-L-prolyl-L-proline

L-alanyl-L-prolyl-L-proline benzyl ester hydrochloride (2.46 g, 6.0 m mole) was dissolved in methylene dichloride (20 ml) and triethyl amine (1.34 g, 13.2 m mole) was added thereto while cooling to −10° C. Acetic acid anhydride (0.67 g, 6.6 m mole) methylene dichloride (10 ml) solution was added thereto while cooling at −10° C. After stirring overnight at room temperature, methylene dichloride (130 ml) was added thereto, and the thus obtained mixture was washed with 1N hydrochloric acid (100 ml), water (100 ml) 5% aqueous sodium bicarbonate (100 ml), and water (100 ml) in order. The methylene dichloride phase was dried over anhydrous sodium sulfate, and the solvent was distilled off under reduced pressure to give an oily residue (2.48 g).

The oily residue was dissolved in 50% aqueous methanol (30 ml) and 5% palladium-carbon (0.5 g) was added thereto as a catalyst, and then hydrogen was passed through the solution for 2 hours. The catalyst was separated by filtration and the solvent was distilled off under reduced pressure to give a glassy residue. Thus given residue was recrystallized with methanol-ether to give N-acetyl-L-alanyl-L-prolyl-L-proline (1.70 g).

NMR spectrum [CDCl$_3$, Internal standard: TMS]: 1.33 ppm (d, 3H), 1.70~2.45 ppm (m, 8H), 1.96 ppm (s, 3H), 3.27~3.92 ppm (m, 4H), 4.40~4.89 ppm (m, 3H), 5.88~6.88 ppm (br, 2H).

TLC [Ethyl acetate:Methanol=1:1; Iodine] Rf=0.2.
TLC [Ethyl acetate:Methanol+1:1; Iodine] Rf=0.2.
Mass spectrum [FAB mode] M+H=326.

EXAMPLE 4

Synthesis of N-propionyl-L-alanyl-L-prolyl-L-proline

L-alanyl-L-prolyl-L-proline benzyl ester hydrochloride (2.4 g. 6.0 m mole) was dissolved in methylene dichloride (20 ml) and triethyl amine (1.34 g, 13.2 m mole) was added thereto while cooling at −10° C., and propionic acid anhydride (0.85 g 6.6 m mole) methylene dichloride (10 ml) solution was added dropwise thereto at a temperature of −10° C. The thus obtained mixture was stirred overnight at room temperature and methylene dichloride (130 ml) was added thereto, and then washed with 1N hydrochloric acid (100 ml), water (100 ml), 5% aqueous sodium bicarbonate (100 ml), and water (100 ml). The methylene dichloride phase was dried over anhydrous sodium sulfate, and the solvent was distilled off under reduced pressure to give an oily residue (2.58 g).

The thus obtained oily residue was dissolved in 50% aqueous methanol (30 ml) and hydrogen was passed through the solution in the presence of 5% palladium-carbon (0.5 g) as a catalyst for 2 hours. The catalyst was separated by filtration and the solvent was distilled off under reduced pressure to give a glass residue. The residue was recrystallized with methanolether to give N-propionyl-L-alanyl-L-prolyl-L-proline crystals (1.71 g).

NMR spectrum [CDCl$_3$, Internal standard: TMS]: 1.13 ppm (t, 3H), 1.33 ppm (d, 3H), 1.72~2.45 ppm (m, 10H), 3.35~3.94 ppm (m, 4H), 4.45~4.90 ppm (m, 3H), 5.73~6.90 ppm (br, 2H).

TLC [Ethyl acetate:Methanol=1:1 Iodine] Rf=0.34.
Mass spectrum [FAB mode] M+H=340.

EXAMPLE 5

Synthesis of N-picolinoyl-L-alanyl-L-prolyl-L-proline

L-alanyl-L-prolyl-L-proline benzyl ester hydrochloride (2.05 g. 5 m mole) was dissolved in chloroform (20 ml) and triethyl amine (0.51 g, 5 m mole), 1-hydroxybenzotriazole (0.67 g, 5 m mole) picolic acid (0.73 g, 6.0 m mole) and 1-(3-dimethylaminopropil)-3-ethylcarbodiimide hydrochloride (0.96 g. 5 m mole) were added thereto while cooling at −15° C., and the thus obtained mixture was stirred for 1 hour at a temperature of less than 0° C. and overnight at room temperature. Chloroform (100 ml) was added to the solution, and the thus obtained mixture was washed 5% aqueous sodium bicarbonate (100 ml), and water (100 ml) in order The chloroform phase was dried over anhydrous sodium sulfate and the solvent was distilled off under reduced pressure to give an oily residue (2.36g). The residue purified by column chromatography (silica gel, developing solvent; ethyl acetate: methanol=20:1) to give N-picolinol-L-alanyl-L-prolyl-L-proline benzylester (1.70 g). This product was dissolved in methanol (30 ml) and hydrogen gas was passed through the solution for 3 hours in the presence of 5% palladium-carbon (0.5 g) as a catalyst. The catalyst was separated by filtration, and the solvent was distilled off under reduced pressure to give a glassy residue. The residue was recrystallized with methanol-ether-petroleum ether to give N-picolinoyl-L-alanyl-L-prolyl-L-proline (1.10 g).

NMR spectrum [CDCl$_3$, Internal standard: TMS]: 1.50 ppm (d, 3H), 1.80~2.43 ppm (m, 8H), 3.35~4.00 ppm (m, 4H), 4.46~4.79 ppm (m, 2H), 4.95 ppm (q, 1H, 6.85~7.45 ppm (m, 2H), 7.75 ppm (t, 1H), 8.08 ppm (d, 1H), 8.50 ppm (d, 1H), 8.63 ppm (d, 1H).

TLC [Ethyl acetate:Methanol=1:1; Iodine] Rf=0.23.
Mass spectrum [FAB mode] M+H=389.

EXAMPLE 6

Synthesis of N-(2- thenoyl)-L-alanyl-L-prolyl-L-proline

L-alanyl-L-prolyl-L-proline (2.83 g. 10 m mole) was dissolved in water-dioxane (2:1, 30 ml) and the solution was adjusted to pH 10 with 1N aqueous sodium hydroxide. 2-thenoylchloride(1.47 g. 10 m mole) dioxane (10 ml) solution was added dropwise thereto while stirring and cooling with ice while maintaining a pH value range of 9.5-10 with 1N aqueous sodium hydroxide. After that, the solution was stirred for 3 hours at room temperature. To this solution, water (30 ml) and ethyl acetate (150 ml) were added and the solution was adjusted to pH 2 under vigorous agitation. An aqueous phase and an ethyl acetate phase were separated and the aqueous phase was extrated again with ethyl acetate (100 ml). The ethyl acetate phase as separated previously, was mixed with the ethyl acetate as extracted thereafter, and the thus obtained solution was dried over anhydrous sodium sulfate. From the solution the solvent was distilled off under reduced pressure to give a glassy residue (3.17 g). This product was recrystallized with ethyl acetate carbon tetrachloride to give N-(2-thenoyl)-L-alanyl-L-prolyl-L-proline (1.18 g).

NMR spectrum [CDCl$_3$, Internal standard TMS]: 1.44 ppm (d,3H), 1.70~2.45 ppm (m,8H), 3.35~4.00 ppm (m,4H), 4.40~4.73 ppm (m,2H), 4.83 ppm (q,1H), 6.96 ppm (t,1H), 7.23 ppm (d,1H), 7.33~7.60 ppm (m,2H), 7.88 ppm (s,1H).

TLC [Ethyl acetate:Methanol=1:1, Iodine] Rf=0.31.

Mass spectrum [FAB mode] M+H=394.

EXAMPLE 7

Synthesis of N-(2-furoyl)-L-alanyl-L-prolyl-L-proline

L-alanyl-L-prolyl-L-proline (2.83g, 10 m mole) was dissolved in water-dioxane (2:1, 30 ml) and the solution was adjusted to pH 10 with 1N aqueous sodium hydroxide. 2-Furoylchloride (1.31 g, 10 m mole) dioxane (10 ml) solution was added dropwise thereto while stirring and cooling with ice while maintaining a pH range of 9.5–10 with 1N aqueous sodium hydroxide, and then the mixture was stirred for 3 hours at room temperature. The solution was adjusted to pH 2 with 1N hydrochloric acid, or concentrated under reduced pressure, and extracted with two 30 ml portions of ethyl acetate. The thus obtained ethyl acetate phase was dried over anhydrous sodium sulfate and the solvent was distilled off under reduced pressure to give a glassy residue (2.47 g). This product was recrystallized with ethyl acetate to give N-(2-furoyl)-L-alanyl-L-prolyl-L-proline (1.48 g)

NMR spectrum [CDCl$_3$, Internal standard: TMS]: 1.45 ppm (d,3H), 1.76~2.45 ppm (m,8H), 3.37~3.97 ppm(m,4H), 4.45~4.73 ppm (m,2H), 4.84 ppm (q,1H), 6.39 ppm (q,1H), 7.02 ppm (d,1H), 7.20 ppm (d,1H), 7.36 ppm (s,1H), 8.14~9.03 ppm (br,1H), TLC [Ethyl acetate:Methanol=1:1; Iodine] Rf=0.26.

Mass spectrum [FAB mode] M+H=378.

EXAMPLE 8

Synthesis of N-phthaloyl-L-alanyl-L prolyl-L-proline

L-alanyl-1-prolyl-L-proline (2.83 g. 10 m mole) was dissolved in water (20 ml) in which sodium carbonate (1.06 g, 10 m mole) had been dissolved. To the solution dioxane (10 ml) was added, and then a N-carboethoxyphthalimide (2.19 g, 10 m mole)-dioxane (10 ml) solution was added dropwise. The solution was stirred for 2 hours at room temperature and washed with ethyl acetate (50 ml). To the solution, water (50 ml) and ethyl acetate (150 ml) were added and the solution was adjusted to pH 2 with 1N hydrochloric acid while stirring vigorously. An ethyl acetate phase was separated, dried over anhydrous sodium sulfate and the solvent was distilled off under reduced pressure to give the residue The residue was recrystallized with ethyl acetate-ether to give N-phthaloyl-L-alanyl-L-prolyl-L-proline (1.01 g).

NMR spectrum [CDCl$_3$, Internal standard: TMS]: 1.68 ppm (d,3H), 1.70~2.46 ppm (m,8H), 3.12~3.90 ppm (m,4H), 4.50~4.68 ppm (m,2H), 4.99 ppm (q, 1H), 6.65~7.35 ppm (br,1H), 7.52~7.86 ppm (m,4H).

TLC [Ethyl acetate:Methanol=1:1, Iodine] Rf=0.34.

Mass spectrum [FAB mode] M+H=414.

Example 9

Synthesis of N-(benzylthio) thiocarbonyl-L-alanyl-L-prolyl-L-proline L-arginine salt (a) N-(benzylthio) thiocarbonyl-L-alanyl-L-prolyl-L-proline.

L-alanyl-L-prolyl-L-proline (2.83 g, 10 m mole) was dissolved in water-dioxane (2:1, 15 ml), and triethyl amine (2.13 g, 21 m mole) was added thereto. To the solution, carbon disulfide (0.76 g, 10 m mole)-dioxane (5 ml) solution was added dropwise. After completion of the addition, the solution was stirred for 1 hour at room temperature. Thereafter, benzyl bromide (1.71 g, 10 m mole) was added thereto; and the mixture was stirred overnight at room temperature, and then water (100 ml) and ethyl acetate (150 ml) were added thereto. The solution was adjusted to pH2 with 1N hydrochloric acid while stirring vigorously. The ethyl acetate phase was separated and dried over anhydrous sodium sulfate, and then the solvent was distilled off under reduced pressure to give a glassy residue. The residue was recrystallized with ethyl acetate-n-hexane to give N-(benzylthio)thiocarbonyl-L-alanyl-L-prolyl-L-proline (2.33 g).

NMR spectrum [CDCl$_3$, Internal standard TMS]: 1.47 ppm (d,3H), 1.75~2.40 ppm (m,8H), 3.30~3.97 ppm (m,4H), 4.33~4.71 ppm (m,2H), 4.42 ppm (s,2H), 5.53 ppm (t,1H), 6.64~7.25 ppm (br,1H), 7.22 ppm (s,5H), 7.99 ppm (d,1H).

TLC [Methanol:Acetic acid=20:1; Spraying of 25% hydrobromic acid acetic acid solution and ninhydrin, and heating] Rf=0.76.

Mass spectrum [FAB mode] M+H=450.

(b) N-(benzylthio)thiocarbonyl-L-alanyl-L-prolyl-L-proline L-arginine salt

N-(benzylthio)thiocarbonyl-L-alanyl-L-prolyl-L-proline (0.90 g, 2 m mole) was dissolved in L-arginine (0.35 g, 2 m mole) water (30 ml) solution, and the thus obtained solution was freeze-dried to give N-(benzylthio)thiocarbonyl-L-alanyl-L-prolyl-L-proline L-arginine salt (1.22 g).

EXAMPLE 10

Synthesis of N-(3-carboxypropanoyl)-L-alanyl-L-prolyl-L-proline

L-alanyl-L-prolyl-L-proline methylester hydrochloride (3.34 g, 10 m mole) was methylene dichloride (30 ml) and triethyl amine (2.23 g, 22 m mole) was added thereto while cooling to −10° C. An ethylsuccinoyl chloride (1.98 g, 12 m mole)-methylene dichloride (10 ml) solution was added dropwise thereto while cooling at −10° C. The mixture was stirred overnight at room temperature and methylene dichloride (100 ml) was added thereto. The solution was washed with 5% aqueous sodium bicarbonate (50 ml), water (50 ml), 1N hydrochloric acid (50 ml) and water (50 ml) in order. A methylene dichloride layer was dried over anhydrous sodium sulfate and the solvent was distilled off under reduced pressure to give an oily residue (4.08 g).

The thus obtained residue was dissolved in methanol (10 ml), and 1N aqueous sodium hydroxide (20 ml) was added thereto. The mixture was stirred for 2 hours at 35° C. The solution was passed through the column with "Dowex 50W-X4 (H+ type)". Thus obtained solution was mixed with the washings of the column, concentrated under reduced pressure, and freeze-dried to give N-(3-carboxypropanoyl)-L-alanyl-L-prolyl-L-proline (2.65 g).

NMR spectrum [CDCl$_3$, Internal standard:TMS]: 1.33 ppm (d,3H), 1.65~2.35 ppm (m,8H), 2.36~2.70 ppm (m,4H), 3.25~3.70 ppm (m,4H), 4.22~4.80 ppm (m,3H), 5.50~7.10 ppm (br,2H), 6.94 ppm (d,1H).

TLC [Ethyl acetate:Methanol=1:1; Iodine] Rf=0.10.

Mass spectrum [FAB mode] M+H=384.

EXAMPLE 11

Synthesis of N-benzylsulfonyl-L-alanyl-L-prolyl-L-proline L-arginine salt (a) N-benzylsulfonyl-L-alanyl-L-prolyl-L-proline N-alanyl-L-prolyl-L-proline (3.00 g, 10.6 m mole) was dissolved in 1N aqueous sodium hydroxide (21.2 ml, 21.2 m mole), and benzylsulfonylchloride (2.02 g, 10.6 m mole)-ether (10 ml) solution was added dropwise thereto while stirring and cooling with ice over 15 minutes. Thus obtained reaction solution was further stirred for 3 hours at room temperature, and the ether layer was separated. The water layer was washed with ether (10 ml) again. The water layer was mixed with ethyl acetate (20 ml), and then adjusted to pH 1.0 with 6N hydrochloric acid while stirring. The ethyl acetate layer was separated, and the water layer was further extracted with ethyl acetate (20 ml). The ethyl acetate layers were combined and washed with 10% aqueous sodium chloride (20 ml), and dried over anhydrous sodium sulfate. The ethyl acetate was removed by distillation under reduced pressure therefrom. Ether was added to the syrupy residue as produced above to effect crystallization. The thus produced crystals were obtained by filtration and washed sufficiently with ether, and dried under reduced pressure to give white crystals of N-benzylsulfonyl-L-alanyl-L-prolyl-L-proline (1.41 g).

NMR spectrum [CDCl$_3$, Internal standard: TMS]: 1.21 ppm (d, 3H), 1.70~2.45 ppm (m, 8H), 2.98~3.90 ppm (m, 4H), 4.17 ppm (s, 2H), 4.22~4.75 ppm (m, 3H), 5.63 ppm (d, 1H), 7.28 ppm (s, 5H), 9.00 ppm (s, 1H).

TLC [Ethyl acetate: Methanol=1:1; Iodine] Rf=0.52.

Mass spectrum [FAB mode] M+H=438.

(b) N-benzyl sulfonyl-L-alanyl-L-prolyl-L-proline L-arginine salt

N-benzylsulfonyl-L-alanyl-L-prolyl-L-proline (1.00 g, 2.29 m mole) and L-arginine (0.399 g, 2.29 m mole) were added to water (50 ml) and stirred for 1 hour at room temperature to make a homogeneous solution. The solution was filtered and the thus obtained filtrate was freeze-dried to give N-benzylsulfonyl-L-alanyl-L-prolyl-L-proline L-arginine salt (1.30 g).

EXAMPLE 12

Synthesis of N-ethanesulfonyl-L-alanyl-L prolyl-L-proline (a) N-ethanesulfonyl-L-alanyl-L-prolyl-L-proline benzylester L-alanyl-L-prolyl-L-proline benzylester hydrochloride (4.09 g, 10.0 m mole) was added to methylene dichloride (40 ml) and triethyl amine (2.02 g, 20.0 m mole), was added thereto while stirring and cooling with ice. After that, ethanesulfonyl chloride (1.29 g, 10.0 m mole)-methylene dichloride (10 ml) solution was added dropwise over 1 hour thereto. The reaction solution was allowed to stand overnight at room temperature and then washed with two 20 ml portions of hydrochloric acid, 10% aqueous sodium chloride (20 ml), two 20 ml portions of 10% aqueous sodium bicarbonate and 10% aqueous sodium chloride (20 ml) in order. A methylene dichloride layer was dried over anhydrous sodium sulfate and the solvent was distilled off under reduced pressure to give a syrupy N-ethanesulfonyl-L-alanyl-L-prolyl-L-proline benzylester (3.85 g).

TLC [Ethyl acetate:Methanol=1:1; Iodine] Rf=0.36.

(b) N-ethanesulfonyl-L-alanyl-Lprolyl-L-proline.

N-ethanesulfonyl-L-alanyl-L-prolyl-L-proline benzylester (2.00 g, 4.29 m mole) was dissolved in a mixture of methanol (10 ml) and water (10 ml), and then hydrogen gas was passed through the solution in the presence of 5% palladium carbon for 1.5 hours at room temperature. Cellite was added to the reaction solution and the solution was filtered and this operation was repeated again. The catalyst was completely removed and the filtrate was concentrated under reduced pressure. The thus produced crystals were obtained by filtration, washed sufficiently with ethyl acetate, and then dried under reduced pressure to give white crystals of N-ethanesulfonyl-L-alanyl-L-prolyl-L-proline (1.17 g).

NMR spectrum [CDCL$_3$, Internal standard: TMS]: 1.20~1.57 ppm (m, 5H), 1.80~2.45 ppm (m, 8H), 2.93 ppm (q, 2H), 3.36~3.95 ppm (m, 4H), 4.24~4.75 ppm (m, 3H), 5.72 ppm (d, 1H), 8.28 ppm (s, 1H).

TLC [Ethyl acetate: Methanol=1:1; Iodine] Rf=0.36.

Mass spectrum [FAB mode] M+H=376.

EXAMPLE 13

Synthesis of N-benzoyl-L-alanyl-L-prolyl-L-proline

L-alanyl-L-prolyl-L-proline (3.00 g, 10.6 m mole) was dissolved in 1N aqueous sodium hydroxide (21,2 ml, 21.2 m mole) and benzoylchloride (1,49 g, 10.6 m mole)-ether (10 ml) homogeneous solution was added dropwise thereto over 30 minutes while stirring and cooling with ice. The thus obtained solution was stirred for 4 hours at room temperature and the reaction solution having a pH value of 10, was washed with two 20 ml portions of ether. A water layer was adjusted to pH 1.0 with 6N hydrochloric acid and extracted with two 30 ml portions of ethyl acetate. The ethyl acetate layer was washed with 10% aqueous sodium chloride and dried over anhydrous sodium sulfate. The solvent was removed therefrom by distillation under reduced pressure. To the obtained syrupy residue ether was added to effect crystallization and the produced crystals (yield: 2.10 g) were obtained on the paper filter.

The crystals were dissolved in ethyl acetate (30 ml) and the solution was filtered. To the solution ether was added to cause turbidity and the mixture was left overnight in a refrigerator. The produced crystals were isolated by filtration, washed with ether and petroleum ether, and dried under reduced pressure to give white crystals of N-benzoyl-L-alanyl-L-prolyl- L-proline (1.01 g).

NMR spectrum [CDCl$_3$, Internal standard: TMS]: 1.48 ppm (d, 3H), 1.80~2.37 ppm (m, 8H), 3.40~4.01 ppm (m, 4H), 4.46~4.77ppm (m, 2H), 4.90 ppm (t, 1H), 7.12~7.53 ppm (m, 4H), 7.60~7.87 ppm (m, 2H), 8.40 ppm (s, 1H).

TLC [Ethyl acetate: Methanol=1:1; Iodine] Rf=0.36.

Mass spectrum [FAB mode] M+H =388.

EXAMPLE 14

Synthesis of N-phenylacetyl-L-alanyl-L-prolyl-L-proline

L-alanyl-L-prolyl-L-proline (3.00 g, 10.6 m mole) and phenyl acetyl chloride (1.64 g, 1.06 m mole) were reacted and the reaction solution was treated in the same manner as in the preparation method of the above mentioned N-benzoyl-L-alanyl-L-prolyl-L-proline.

The reaction products were extracted with ethyl acetate and the ethyl acetate solution (40 ml) was dried over anhydrous sodium sulfate and left for 2 days in a refrigerator to produce needle-crystals. The crystals were obtained by filtration and dried to give the desired product (2.27 g). These crystals were recrystallized with ethyl acetate (200 ml) to give N-phenylacetyl-L-alanyl-L-prolyl-L-proline (1.27 g). NMR spectrum [CDCl$_3$, Internal standard: TMS]: 1.29 ppm (d, 3H), 1.78~2.42 ppm (m, 8H), 3.37~3.90 ppm (m, 4H), 3.47 ppm (s, 2H), 4.39~4.87 ppm (m, 3H), 6.62 ppm (d, 1H), 7.19 ppm (s, 5H), 8.39 ppm (s, 1H), TLC [Ethyl acetate: Methanol=1:1; Iodine] Rf=0.34.

Mass spectrum [FAB mode] M+H=402.

EXAMPLE 15

Synthesis of N-benzyloxycarbonyl-L-alanly-L-prolyl-L-proline L-arginine salt (a) N-benzyloxycarbonyl-L-alanyl-L-prolyl-L-proline To N-benzyloxycarbonyl-L-alanyl-L-prolyl-L-proline methylester (4.31 g, 10 m mole), 1.5 N aqueous sodium hydroxide (10 ml, 15 m mole) was added and the mixture was stirred for 2 hours at 30° C. The solution was adjusted to pH 2.5 with 1N hydrochloric acid, and then extracted with two 50 ml portions of 1,2-dichloroethane. The thus obtained 1,2-dichloroethane layer was concentrated under reduced pressure. The residue was recrystallized with acetone-water to give N-benzyloxycarbonyl-L-alanyl-L-prolyl-L-proline (3.68 g).

NMR spectrum [CDCl$_3$, Internal Standard: TMS]: 1.33 ppm (d, 3H), 1.72~2.30 ppm (m, 8H), 3.30~3.85 ppm (m, 4H), 4.22~4.72 ppm (m, 3H), 5.00 ppm (s, 2H), 5 74 ppm (d, 1H), 7.27 ppm (s, 5H).

TLC [Ethyl acetate: Methanol=1:1; Spraying of 25% hydrobromic acid acetic acid solution and ninhydrin, and heating] Rf=0.44.

Mass sepctrum [FAB mode] M+H=418.

(b) N-benzyloxycarbonyl-L-alanyl-L-prolyl-L-proline-L-arginine salt

N-benzyloxycarbonyl-L-alanyl-L-prolyl-L-proline (1.00 g, 2.40 m mole) was dissolved in L-arginine (0.41 8 g, 2.40 m mole) - water (50 ml) solution and the thus obtained solution was freeze-dried to obtain N-benzyloxycarbonyl-L-alanyl-L-prolyl-L-proline L -arginine salt (1.40 g).

EXAMPLE 16

Synthesis of N-t-butyloxycarbonyl-L-alanyl-L-prolyl-L-proline.

N-t-butyloxycarbonyl-L-alanyl-L-prolyl-L-proline benzylester (5.0 g, 10.6 m mole) was dissolved in methanol (100 ml) and hydrogen gas was passed through the solution in the presence of the palladium carbon as a catalyst for 3 hours. The catalyst was removed by filtration and the solvent was distilled off under reduced pressure. Thus obtained was dissolved in water and the solution was freeze-dried to give N-t-butyloxycarbonyl-L-alanyl-L-prolyl-L-proline (4.04 g).

NMR spectrum [CDCl$_3$, Internal standard TMS: ]: 1.33 ppm (d, 3H), 1.42 ppm (s, 9H), 1.80~2.42 ppm (m, 8H), 3.40~3.89 ppm (m, 4H), 4.30~4.73 ppm (m, 3H), 5.26 ppm (d, 1H), 6.22 ppm (s, 1H).

TLC [n-Butanol:Acetic acid:Water=2:1:1; Spraying of 25% hydrobromic acid acetic acid solution and ninhydrin and heating] Rf=0.69.

Mass spectrum [FAB mode] M+H=384.

EXAMPLE 17

Synthesis of N-phenylcarbamoyl-L-alanyl-L-prolyl-L-proline L-arginine salt (a) N-phenylcarbamoyl-L-alanyl-L-prolyl-L-proline L-alanyl-L-prolyl-L-proline (3.00 g, 10.6 m mole) was dissolved in 1N aqueous sodium hydroxide (10.6 ml, 10.6 m mole), and phenylisocyanate (1.89 g, 15.9 m mole) was gradually added thereto while stirring and coating with ice. After that, the reaction solution was stirred overnight at room temperature. The pH value of the solution was about 7 and white crystals were given in the solution. The solution was adjusted to pH 12 with 1N aqueous sodium hydroxide and the insoluble matters were filtered off. The filtrate was washed with two 50 ml portions of ether and 6N hydrochloric acid was added thereto to adjust the pH value to 1.0. The solution was extracted with two 100 ml portions of ethyl acetate in order to separate the products. The ethyl acetate layer was washed with 10% aqueous sodium chloride, dried over anhydrous sodium sufate, and concentrated under reduced pressure. To the thus concentrated matter with crystals, ether was added to effect further crystallization. The crystals were obtained by filtration and dried to give N-phenylcarbamoyl-L-alanyl-L-prolyl-L-proline (2.50 g).

NMR spectrum [CDCl$_3$+DMSO-d$_6$, Internal Standard: TMS]: 1.30 ppm (d, 3H), 1.67~2.33 ppm (m, 8H), 3.30~3.91 ppm (m, 4H), 4.22~4.73 ppm (m, 3H), 6.29 ppm (d, 1H), 6.67~7.35 ppm (m, 5H), 8.35 ppm (s, 1H).

TLC [Methanol:Acetic acid=9:1; Iodine] Rf=0.88.

Mass spectrum [FAB mode] M+H=403.

(b) N-phenylcarbamoyl-L-alanyl-L-prolyl-L-proline L-arginine salt

N-phenylcarbamoyl-L-alanyl-L-prolyl-L-proline (1.00 g-2.49 m mole) was dissolved in a solution of L-arginine (0.43 g, 2.49 m mole) in water, and the thus obtained solution was freeze-dried to give N-phenylcarbamoyl-L-alanyl-L-prolyl-L-proline L-arginine salt (1.38 g).

EXAMPLE 18

Synthesis of N-phenylthiocarbamoyl-L-alanyl-L-prolyl-L-proline L-arginine salt (a) N-phenylthiocarbamoyl-L-alanyl-L-prolyl-L-proline L-alanyl-L-prolyl-L-proline (3.00 g, 10.6 m mole) was reacted with phenylisothiocyanate (2.15 g, 15.9 m mole) and then the reaction solution was treated in the same manner as the synthetic method of the N -phenylcarbamoyl-L-alanyl-L-prolyl-L-proline.

From the extraction solution with ethyl acetate, the solvent was removed by distillation under reduced pressure, and ether was added thereto. The thus produced crystals were obtained by filtration, washed and dried to give N-phenylthiocarbamoyl-L-alanyl-L-prolyl-L-proline (2.65 g).

NMR spectrum [CDCl$_3$, Internal standard: TMS]: 1.38 ppm (d, 3H), 1.67~2.36 ppm (m, 8H), 3.24~4.05 ppm (m, 4H), 4.20~4.74 ppm (m, 2H), 5.15 ppm (t, 1H), 7.24 ppm (s, 5H), 8.45 ppm (s, 1H), 9.67 ppm (s,1H).

TLC [Methanol:Acetic acid=9:1; Iodine] Rf=0.76.
Mass spectrum (FAB mode) M+H=419.

(b) N-phenylthiocarbamoyl-L-alanyl-L-prolyl-L-proline L-arginine salt

The object product of N-phenylthiocarbamoyl-L-alanyl-L-prolyl-L-proline L-arginine salt (1.38 g) was obtained on the basis of the above mentioned method using N-phenylthiocarbamoyl-L-alanyl-L-prolyl-L-proline (1.00 g, 2.49 m mole) and L-arginine (0.433 g, 2.49 m mole) as a starting material.

EXAMPLE 19

Synthesis of L-prolyl-L-alanyl-L-prolyl-L-proline

L-alanyl-L-prolyl-L-proline benzylester hydrochloride (2.46 g, 6 m mole), benzyloxcarbonyl-L-proline (1.65 g, 6.6 m mole) and 1-hydroxybenzotriazole (0.9 g, 6.6 m mole) were dissolved in dimethylformamide (6 ml) and 1-(3-dimethylaminopropyl)-3-ethylcarbodiimide (1.2 ml, 6.6 m mole) was added thereto at −15° C. The mixture was stirred for 16 hours at room temperature and to the reaction solution, ethyl actate was added. The solution was washed with 1N hydrochloric acid, 5% aqueous sodium bicarbonate and water in order. The ethyl acetate layer was dried over anhydrous sodium sulfate and the solvent was distilled off under reduced pressure. The thus obtained oily residue was dissolved in methanol-water (4:1, 25 ml and hydrogen gas was passed through the solution in the presence of palladium carbon as a catalyst for 2 hours. The catalyst was separated by filtration and the solvent was distilled off under reduced pressure. The thus obtained residue was recrystallized with methanol-ether to give L-prolyl-L-alanyl-L-prolyl-L-proline (1.48 g).

Elementary analysis:
Found C 52.86%, H 7.85%, N 13.01%,
Calculation C 53.01%, H 7.96%, N 13.02%, as C$_{18}$H$_{28}$N$_4$O$_5$.CH$_3$OH.H$_2$O.

Amino acid analysis [Hydrolysis with 6N hydrochloric acid]
Ala:Pro=1.00:2.94.

TLC [n-Butanol:Acetic acid:Water=4:1:5 (upper phase); Spraying of 25% hydrobromic acid acetic acid solution and ninhydrin, and heating] Rf=0.2.
Mass spectrum [FAB mode] M+H=381.

EXAMPLE 20

Synthesis of glycyl-L-alanyl-L-prolyl-L-proline

L-Alanyl-L-prolyl-L-proline benzylester hydrochloride (2.46 g, 6 m mole) was dissolved in dimethylformamide (10 ml) and triethyl amine (0.48 ml, 6 m mole) was added thereto while cooling to neutralize the solution, and then benzyloxycarbonylglycine N-hydroxysuccinimideester (2.02 g, 6.6 m mole) was added thereto. The reaction solution was stirred for 2 days while it had been adjusted to pH around 7 with triethyl amine, and ethyl acetate (150 ml) was added thereto and the solution was washed with 1N hydrochloric acid, 5% aqueous sodium bicarbonate and water in order. The ethyl acetate layer was dried over anhydrous sodium sulfate and the solvent was distilled off under reduced pressure to give a residue. The thus obtained residue was recrystallized with ethyl acetate to give N-benzyloxycarbonyl glycyl-L-alanyl-L-prolyl-L-proline benzylester (1.3 g). The product as produced above (1.2 g) was dissolved in methanol (50 ml) and then, hydrogen gas was passed through the solution in the presence of palladium-carbon as a catalyst for 3 hours. The catalyst was separated by filtration and the solvent was distilled off. The thus obtained residue was recrystallized with methanol-ether to give glycyl-L-alanyl-L-prolyl-L-proline (688 mg).

Elementary analysis: Found C 49.34%, H 7.93%, N 14.73%, Calculation C 49.68%, H 7.71%, N 14.48%, as C$_{15}$H$_{24}$N$_4$O$_5$.CH$_3$OH.0.8H$_2$O.

Amino acid analysis [Hydrolysis with 6N hydrochloric acid]
Gly:Ala:Pro=1.00:0.97:1.96.

TLC [n-Butanol:Acetic acid:Pyridine:Water=15:3:12:10; Spraying of 25% hydrobromic acid acetic acid solution and ninhydrin, and heating] Rf=0.30.
Mass spectrum [FAB mode] M+H=341.

EXAMPLE 21

Synthesis of L-pyroglutamyl-L-alanyl-L-prolyl-L-proline

L-alanyl-L-prolyl-L-proline benzylester hydrochloride (2.46 g, 6 m mole) was dissolved in dimethylformamide (10 ml, and triethylamine (0.84 ml, 6m mole) was added thereto under cooling to neutralize it and then benzyloxycarbonyl-L-pyroglutamic acid N-hydroxysuccinimide ester (2.38 g, 6.6 m mole) was added thereto. The mixture was stirred for 2 days while the solution had been adjusted to a pH of about 7 with triethylamine and then ethyl acetate (150 ml) was added thereto. The solution was washed with 1N hydrochloric acid, 5% aqueous sodium bicarbonate and water in order. The ethyl acetate layer was dried over anhydrous sodium sulfate and the solvent was distilled off under reduced pressure. To the thus obtained residue, n-hexane was added to form a powder. This powder was purified by column chromatography. (Silica gel, developing solvent; chloroform:ethanol:ethyl acetate=5:1:5). The fractions of the main ingredient were collected together and then concentrated. To the residue, n-hexane was added to precipitate the powder. They were dissolved in methanol (50 ml) and then hydrogen gas passed through the solution in the presence of palladium-carbon as a catalyst for 4 hours. The catalyst was separated by filtration and the solvent was distilled off. The thus obtained residue was recrystallized with methanol-ether to give L-pyroglutamyl-L-alanyl-L-prolyl-L-proline (880 mg).

Elementary analysis: Found C 52.04%, H 7.30%, N 12.63%, Calculation C 51.99%, H 7.00%, N 12.76%, as C$_{18}$H$_{25}$N$_4$O$_6$.CH$_3$OH.0.75H$_2$O.

Amino acid analysis [Hydrolysis with 6N hydrochloric acid]
Glu:Ala:Pro=1.00:0.98:1.96.

TLC [n-Butanol:Acetic acid:Water=4:1:5 (upper phase); Spraying of 25% hydrobromic acid acetic acid solution and ninhydrin, and heating] Rf=0.23.
Mass spectrum [FAB mode] M+H=395.

EXAMPLE 22

Synthesis of L-phenylalanyl-L-alanyl-L-prolyl-L-proline

L-alanyl-L-prolyl-L-proline benzylester hydrochloride (2.46 g, 6 m mole) was dissolved in dimethylformamide (10 ml), and triethylamine (0.84 ml, 6 m mole) was added thereto under cooling to neutralize it. Benzyloxycarbonyl-L-phenylalanine N-hydroxysuccinimide ester (2.62 g, 6.6 m mole) was added thereto. The reaction solution was stirred for 2 days while it had bean adjusting to pH around 7 with triethylamine, and then ethyl acetate (150 ml) was added thereto. The mixture was washed with 1N hydrochloric acid, 5% aqueous sodium bicarbonate, and water in order. The ethyl acetate layer was dried over anhydrous sodium sulfate and the solvent was distilled off under reduced pressure. The thus obtained residue was recrystallized with ethyl acetate to give N-benzyloxycarbonyl-L-phenylalanyl-L-alanyl-L-prolyl-L-proline benzylester (3.2 g). The product as produced above (3 g) was dissolved in methanol (100 ml) and hydrogen gas was passed through the solution in the presence of palladium-carbon as a catalyst for 5 hours. The catalyst was separated by filtration and the solvent was distilled off from the filtrate. The thus obtained residue was recrystallized with methanolether to give L-phenylalanyl-L-alanyl-L-prolyl-L-proline (1.4 g).

Amino acid analysis [Hydrolysis with 6N hydrochloric acid]
Ala:Pro:Phe=1.00:1.94:0.99.

TLC [n-Butanol:Acetic acid:Water=4:1:5 (upper phase); Spraying of 25% hydrobromic acid acetic acid solution and ninhydrin, and heating] Rf=0.19.

Mass spectrum [FAB mode] M+H=431.

EXAMPLE 23

Synthesis of N-benzyl-L-alanyl-L-prolyl-L-proline

A mixture of L-alanyl-L-prolyl-L-proline (12.83 g, 9.99 m mole), benzaldehyde (5.50 g, 51.8 m mole), zeolite "3A" (20 g), and ethanol (60 ml), was stirred overnight at room temperature. Sodium borohydride (1.609 g, 42.3 m mole) - ethanol (70 ml) suspending solution was added dropwise thereto, and after that, the mixture was stirred for 10 hours. The zeolite was removed by filtration and the filtrate was concentrated under reduced pressure. To the solution, ether was added to effect crystallization. The thus produced crystals were obtained by filtration, washed with three 50 ml portions of ether, then purified with the ion exchange resin "Dowex 50 W-X4", and then recrystallized with ethanol-ether to give N-benzyl-L-alanyl-L-prolyl-L-proline (2.10 g).

NMR spectrum [D$_2$O, Internal standard: DSS]. 1.52 ppm (d, 3H), 1.73~2.50 ppm (m, 8H), 3.24~3.86 ppm (m, 4H), 3.93~4.58 ppm(m, 3H), 4.19 ppm (s, 2H), 7.45 ppm (s, 5H).

TLC [Methanol:Acetic acid=9:1; Spraying of 25% hydrobromic acid acetic acid solution and ninhydrin, and heating] Rf=0.43.

Mass spectrum [FAB mode) M+H=374.

EXAMPLE 24

Synthesis of N,N-dimethyl-L-alanyl-L-prolyl-L-proline

L-alanyl-L-prolyl-L-proline (2.83 g, 9.99 m mole), formalin (37% aqueous solution, 6 ml), 5% palladium carbon (2.5 g) and water (50 ml) were put in the autoclave, and the reaction was carried out under a hydrogen pressure of 50 kg/cm$^2$, at room temperature for 40 hours. The catalyst was removed by filtration, and the filtrate was decolored with active carbon and then purified with the ion exchnge resin "Dowex 50W - X4", and then freeze-dried to give N,N-dimethyl-L-alanyl-L-prolyl-L-proline (1.55 g).

NMR spectrum [D$_2$O, Internal standard: TMS]: 1.50 ppm (d. 3H), 1.70~2.51 ppm (m, 8H), 2.80 ppm (s, 6H), 3.33~3.88 ppm (m, 4H), 4.05~4.44 ppm (m, 3H).

TLC [Methanol:Acetic acid=9:1; Iodine] Rf=0.23.

Mass spectrum [FAB mode] M+H=312.

MEASUREMENT OF CHANGE IN BLOOD PRESSURE

The antihypertensive activities of the amino acid derivatives as prepared above were determined.

As subject animals, there were used 5 spontaneously hypertensive rates (SHR rats) which had been sufficiently trained and confirmed to be hypertensive (mode, the body weight of 400 g) per a sample.

As an instrument for measuring the blood pressure there was used Programmed Electro-Sphygmomanometer PE-300 (Narco Co., U.S.A.), and the blood pressure was indirectly measured on conscious rats.

An aqueous solution of a sample (0.05 m mole/kg) was once force-fed into the stomach by means of a peroneal probe. As a control, the water as deionized was fed to the same animals as above.

The results were shown in Table 1.

TABLE 1

| Sample Example | Systolic Blood Pressure, mm Hg | | | |
|---|---|---|---|---|
| | Value before Administration | Lowest value after administration | Hours after administration | Δ Blood Pressure |
| 1 | 193 | 155 | 8 | −38 |
| 2 | 190 | 154 | 24 | −36 |
| 3 | 201 | 160 | 8 | −41 |
| 4 | 197 | 173 | 8 | −24 |
| 5 | 197 | 175 | 8 | −22 |
| 6 | 202 | 182 | 8 | −20 |
| 7 | 205 | 177 | 8 | −28 |
| 8 | 225 | 207 | 4 | −18 |
| 9 | 216 | 191 | 24 | −25 |
| 11 | 202 | 174 | 8 | −28 |
| 12 | 204 | 159 | 24 | −45 |
| 13 | 220 | 177 | 8 | −43 |
| 14 | 199 | 175 | 8 | −24 |
| 15 | 205 | 172 | 4 | −33 |
| 16 | 194 | 173 | 8 | −21 |
| 17 | 218 | 203 | 24 | −15 |
| 18 | 224 | 211 | 24 | −13 |
| 21 | 219 | 190 | 8 | −29 |

The following additional products were also prepared as indicated.

TABLE 1

| Ex. No. | Product | Ex. No. to which the same reaction was applied | Starting Materials | TLC, Rf Value | Mass Spectrum [FAB mode] (M + H) |
|---|---|---|---|---|---|
| 25 | N—benzoyl-L-isoleucyl- | 3 | L-isoleucyl-L-prolyl-L-proline benzyl | x1 | 430 |

TABLE 1-continued

| Ex. No. | Product | Ex. No. to which the same reaction was applied | Starting Materials | TLC, Rf Value | Mass Spectrum [FAB mode] (M + H) |
|---|---|---|---|---|---|
| | L-prolyl-L-proline | | ester hydrochloride, benzoylchloride N—methylmorpholine | 0.71 | |
| 26 | N—Benzoyl-L-phenylalanyl-L-prolyl-L-proline sodium salt | 3 x2 | L-Phenylalanyl-L-prolyl-L-proline benzylester hydrochloride, benzoylchloride, N—methylmorpholine | x3 0.78 | 486 |
| 27 | N—benzoyl-glycyl-L-prolyl-L-proline | 3 | glycyl-L-prolyl-L-prolinebenzylester hydrochloride, benzoylchloride, N—methylmorpholine | x1 0.64 | 374 |
| 28 | N—benzoyl-L-glutamyl-L-prolyl-L-proline | 3 | γ-benzyl-L-glutamyl-L-prolyl-L-proline benzylester hydrochloride, benzoylchloride, N—methylmorpholine | x3 0.54 | 446 |
| 29 | N—benzyl-L-seryl-L-prolyl-L-proline | 5 | L-seryl-L-prolyl-L-proline benzylester hydrochloride, benzoic acid | x4 0.18 | 404 |
| 30 | N—ethoxycarbonyl-L-isoleucyl-L-prolyl-L-proline sodium salt | 2 | L-isoleucyl-L-prolyl-L-proline benzylester hydrochloride, ethoxycarbonylchloride, N—methylmorpholine | x3 0.78 | 442 |
| 31 | N—ethoxycarbonyl-L-phenylalanyl-L-prolyl-L-proline sodium salt | 2 | L-Phenylalanyl-L-prolyl-L-proline benzylester hydrochloride, ethoxycarbonyl chloride, N—methylmorpholine | x3 0.73 | 454 |
| 32 | N—ethoxycarbonyl-glycyl-L-prolyl-L-proline sodium salt | 2 | glycyl-L-prolyl-L-proline benzylester hydrochloride, ethoxycarbonyl chloride, N—methylmorpholine | x3 0.49 | 364 |
| 33 | N—ethoxycarbonyl-L-glutamyl-L-proline | 3 | γ-benzyl-L-glutamyl-L-prolyl-L-proline benzylester, hydrochloride, ethoxycarboxyl chloride, N—methylmorpholine | x3 0.52 | 414 |
| 34 | N—ethoxycarbonyl-L-arginyl-L-prolyl-L-proline | 3 | $N^g$—Nitro-L-arginyl-L-proline benzylester hydrochloride, ethoxy carbonylchloride, N—methylmorpholine | x3 0.42 | |
| 35 | N—Ethoxycarbonyl-L-seryl-L-prolyl-L-proline | 3 | L-Seryl-L-prolyl-L-proline benzylester hydrochloride, ethoxycarboxylchloride, N—methylmorpholine | x1 0.57 | 372 |
| 36 | N—Ethoxycarbonyl-L-methionyl-L-prolyl-L proline sodium salt | 3 x5 | L-Methionyl-L-prolyl-L-proline benzylester hydrochloride, ethoxycarbonyl chloride N—methylmorpholine | x3 0.63 | 438 |
| 37 | N—ethanesulphonyl-L-isoleucyl-L-prolyl-proline sodium salt | 2 | L-isoleucyl-L-prolyl-L-proline benzylester hydrochloride, ethansulfonyl chloride, triethyl amine | x6 0.67 | 462 |
| 38 | N—ethanesulfonyl-L-phenylalanyl-L-prolyl-L-proline | 5 | N—ethanesulfonyl-L-phenylalanine dicyclohexyl amine salt, L-prolyl-L-proline benzylester hydrochloride | x7 0.68 | 452 |
| 39 | N—ethanesulfonyl-glycyl-L-prolyl-L-proline | 3 | glycyl-L-prolyl-L-proline benzylester hydrochloride, ethanesulfonylchloride, triethylamine | x7 0.56 | 362 |
| 40 | N—ethane sulfonyl-L-glutamyl-L-prolyl-L proline | 3 | α-benzyl-L-glutamyl-L-prolyl-L-proline benzylester hydrochloride, ethansulfonyl chloride, triethyl amine | x7 0.59 | 434 |
| 41 | N—ethane sulfonyl-L-arginyl-L-prolyl-L-proline | 3 | $N^g$—nitro-L-arginyl-L-prolyl-L-proline benzylester hydrochloride, ethanesulfonyl chloride, triethyl amine | x6 0.49 | 461 |
| 42 | N—ethane sulfonyl-L-seryl-L-prolyl-L-proline sodium salt | 2 | L-seryl-L-prolyl-L-proline benzylester hydrochloride, ethanesulfonyl chloride triethyl amine | x7 945 | 414 |
| 43 | N—ethane sulfonyl-L-methionyl-L-prolyl-L-proline | 36 | L-methionyl-L-prolyl-L-proline benzylester hydrochloride, ethanesulfonyl | x6 0.60 | 458 |

In above Table 1, the details of the reaction systems utilized and the solvent systems employed for thin-layer chromatography are explained by matching the designation "x number" in Table 1 with the following descriptions in Table 2.

TABLE 2 x1: Ethyl acetate:Methanol:Acetate acid:Water = 10:10:1:1; Spraying of 25% hydrobromic acid and ninhydrin, and heating.

x2: N—Benzoyl-L-phenylalanyl-L-prolyl-L-proline was obtained by using the same operation as one in Example 3. To N—benzoyl-L-phenylalanyl-L-prolyl-L-proline (1.20 g, 2.58 m mole) and sodium bicarbonate (0.217 g, 2.58 m mole), water (40 ml) was added to neutralize it, and the thus obtained solution was freeze-dried to give N—benzoyl-L-phenylalanyl-L-prolyl-L-proline sodium salt yielding 1.21 g (2.50 m mole; 97%).

x3: n-Butanol:Acetic acid:Pyridine:Water = 4:1:1:2; Spraying of 25% hydrobromic acid and ninhydrine, and heating.

x4: Ethyl acetate; Spraying of 25% hydrobromic acid and ninhydrin, and heating.

x5: N—Ethoxycarbonyl-L-methionyl-L-prolyl-L-proline benzylester was obtained by carrying out the same operation as one in Example 3. A mixture of N—ethoxycarbonyl-L-methionyl-L-prolyl-L-proline benzylester (2.28 g, 4.51 m mole), 1N aqueous NaOH (5.4 ml) and methanol (5 ml) was stirred for 10 hours to allow a reaction. The

TABLE 2-continued solvent was distilled off under reduced pressure, and to the resulting residue water (50 ml) was added. The thus obtained solution was washed three times with ethyl acetate (50 ml). The solution was adjusted to pH 2 in the aqueous layer with 1N hydrochloric acid, and the water was distilled off under reduced pressure. To the residue, methylene dichloride (100 ml) was added, and then insoluble material was removed by filtration. The organic layer was dried over anhydrous sodium sulfate, and the solvent was distilled off under reduced pressure to give N—ethoxycarbonyl-L-methionyl-L-prolyl-L-proline (0.740 g, 1.78 m mole). Next, the same operation as one shown in Example 26 was employed for treating this reaction solution to give the object product as mentioned above yielding 0.766 g (1.75 m mole, 39%).

x6: n-Butanol:Acetic acid:Pyridine:Water = 4:1:1:2; Ammonium molybdate (24 g) and cerium sulfate (1 g) were dissolved in 10% sulfuric acid (500 ml) and the thus obtained aqueous solution is called "molybdenum solution" hereinafter. Spraying of the molybdenum solution and heating.

x7: Ethyl acetate:Methanol:Acetic acid:Water = 10:10:1:1; Spraying of the molybdenum solution and heating.

The following Tables provide NMR characterizations of the designated compounds of the present invention and also the decrease in blood pressure attributed to the use of these compounds as antihypertensives.

| Example | | H—NMR DATA USING TMS AS AN INTERNAL STANDARD |
|---|---|---|
| 25 | CDCl$_3$(TMS) (designated as "a") | 0.95~1.32(m,8H), 1.80~2.40(m,9H) 3.33~4.10(m,4H), 4.45~4.88(m,3H) 7.00(d,1H), 7.18~7.43(m,3H) 7.60~7.82(m,2H) |
| 26 | D$_2$O(TSP) (designated as "b") | 1.70~2.55(m,8H), 2.77~4.99(m,9H) 6.99~7.72(m,11H) |
| 27 | (a) | 1.80~2.45(m,8H), 3.35~4.70(m,8H) 6.62(s,1H), 7.15~7.80(m,5H) |
| 28 | (a) | 1.40~2.62(m,12H), 3.35~4.05(m,4H) 4.28~5.18(m,3H), 7.20~7.45(m,3H) 7.60~8.00(m,5H) |
| 29 | (a) | 1.55~2.28(m,8H), 3.35~4.15(m,6H) 4.30~4.70(,m2H), 4.88~5.17(m,1H) 5.70~(s,1H), 5.97(s,1H) 7.20~7.43(m,4H), 7.50~7.80(m,2H) |
| 30 | (b) | 0.80~1.10(m,8H), 1.20(t,3H) 1.75~2.40(m,7H), 3.40~3.95(m,4H) 4.00~4.30(m,3H), 4.01 (q,2H) |
| 31 | (b) | 1.00~1.31(m,3H), 1.75~2.52(m,8H) 2.60~4.32(m,9H), 3.90(q,2H) 6.97~7.35(m,6H) |
| 32 | (b) | 1.25(t,3H), 1.68~2.60(m,8H) 3.35~4.50(m,6H), 3.95(s,2H) 4.08(q,2H) |
| 33 | (a) | 1.17(t,3H), 1.67~2.55(m,12H) 3.35~3.85(m,4H), 4.00(d,2H) 4.25~4.65(m,3H), 5.82(d.1H) 1.82(s,1H), 8.20(s,1H) |
| 34 | (b) | 1.23(t,3H), 1.50~2.50(m,12H) 3.—3~4.60(m,9H), 4.05(q,2H) |
| 35 | (a) | 1.25(t,3H), 1.90~2.44(m,8H) 3.55~4.80(m,7H), 4.07(q,2H) 5.45(s,1H), 5.55(s,1H) |
| 36 | (b) | 1.20(t,3H), 1.60~2.40(m,10H) 2.10(s,3H), 2.64(t,2H) 3.37~4.65(m,7H), 4.10(q,2H) |
| 37 | (b) | 0.95 to 1.20(m,9H) 1.33 (t,3H) 1.50 to 2.55(m,8H) 3.02 (q,2H) 3.45 to 4.37(m,7H) |
| 38 | (b) | 0.95 to 1.40(m,3H) 2.00 to 2.60(m,8H) 2.75 to 3.98(m,9H) 6.41 (bs, 1H) 7.05 to 7.33(m5H) |
| 39 | (a) | 1.25 to 1.50(m,3H) 0.70 to 2.60(m,8H) 3.02(q,2H) 3.30.to 3.80(m,4H) 3.83(bs,2H) 4.30 to 4.75(m,3H) 5.51(bs,1H) |
| 40 | (a) | 1.20 to 1.55(m,3H) 2.00 to 2.65(m,12H) 2.88 (q,2H) 3.50 to 3.95(m,4H) 4.90 to 5.25(m,3H) 6.10 (d,1H) |
| 41 | (b) | 1.20~1.45(m,3H), 1.50~2.70(m,12H) 2.90(d,2H), 3.10~4.65(m,9H) |
| 42 | (b) | 1.30(m,3H), 1.74~2.65(m,8H) |

-continued

| Example | | H—NMR DATA USING TMS AS AN INTERNAL STANDARD |
|---|---|---|
| 43 | (b) | 3.23(q,2H), 3.48~4.00(m,4H) w3.67(d,2H), 4.15~4.85(m,3H) 1.30(t,3H), 1.75~2.51(m,10H) 2.11(s,3H), 2.70(t,2H) 3.15(q,2H), 3.38~4.81(m,7H) |

| | Systolic Blood Pressure | | | |
|---|---|---|---|---|
| Sample Example No. | Value Before Administration | Lowest Value | Hrs. After Admin. | Δ Blood Pressure |
| 25 | 229 | 201 | 8 | −28 |
| 26 | 228 | 194 | 8 | −34 |
| 27 | 232 | 209 | 8 | −23 |
| 28 | 235 | 196 | 8 | −39 |
| 29 | 214 | 192 | 8 | −22 |
| 30 | 224 | 208 | 4 | −16 |
| 31 | 216 | 199 | 24 | −17 |
| 32 | 215 | 193 | 8 | −22 |
| 33 | 220 | 202 | 8 | −18 |
| 34 | 203 | 192 | 4 | −11 |
| 35 | 220 | 195 | 8 | −25 |
| 36 | 223 | 206 | 8 | −17 |
| 37 | 218 | 194 | 8 | −22 |
| 38 | 235 | 201 | 8 | −34 |
| 39 | 232 | 215 | 8 | −18 |
| 40 | 220 | 202 | 8 | −18 |
| 41 | 204 | 185 | 7 | −19 |
| 42 | 220 | 200 | 24 | −20 |
| 43 | 229 | 198 | 8 | −31 |

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. An amino acid derivative having the formula:

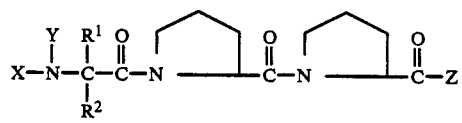

wherein one of X or Y represents an acyl group RCO—, wherein said R is an amino acid residue selected from the group consisting of glycyl, alanyl, valyl, leucyl, isoleucyl, phenylalanyl, methionyl, prolyl, ceryl, threonyl, arginyl, lysyl, histidyl, aspartyl, asparaginyl, tyrosyl, cysteinyl, tryptophyl, and hydroxyprolyl, and the other group is H; $R^1$ and $R^2$ are the same or different from each other, and each represents H, lower alkyl having 1 to 6 carbon atoms, aryl having 6 to 12 carbon atoms, any of which are unsubstituted or substituted by one or more lower alkyl, lower alkoxy, hydroxy, amino, carboxy or mercapto groups; Z represents —OH, RO—, RS—, RNH—, NONH—, RONH—, $RSO_2NH$—, RCONH—, or RCSNH—; and wherein R as defined above for the moiety Z is H, lower alkyl having 1 to 6 carbon atoms, aryl having 6 to 12 carbon atoms or aralkyl having 6 to 12 carbon atoms, any of which are unsubstituted or substituted by one or more lower alkyl, lower alkxoy, hydroxy, amino, carboxy or mercapto groups.

2. The amino acid derivative of claim 1, wherein at least one of the amino acids constituting said derivative is in the L-form.

3. The amino acid derivative of claim 1, wherein R and R40 of either X, Y or Z in the formula each represents an alkyl group of 1 to 6 carbon atoms, an aryl group of 6 to 12 carbon atoms or an aralkyl group of 6 to 12 carbon atoms, all of which are unsubstituted or substituted as described.

4. The amino acid derivative of claim 1, wherein R and R' of either X, Y or Z of the formula each represents a group selected from the group consisting of methyl, ethyl, n-propyl, n-butyl, t-butyl, phenyl, naphthyl, p-tolyl, biphenyl, benzyl, phenethyl, phenylpropyl, carboxymethyl, carboxyethyl, aminomethyl, aminoethyl, hydroxymethyl, hydroxyethyl, mercaptomethyl, mercaptoethyl, aminophenyl, aminobenzyl, hydroxyphenyl, hydroxybenzyl, mercaptophenyl, mercaptobenzyl, cyclopentyl and cyclohexyl.

5. The amino acid derivative of claim 1; wherein R and R' of either X, Y or Z of the formula each represents a group selected from the group consisting of furyl, thienyl, pyrrolyl, pyridyl, quinolyl, thiazolyl, imidazolyl, indolyl, carbazolyl, purinyl, furfuryl, thenyl, pyridylmethyl, indolinyl, pyrrolidinyl and piperidinyl.

6. The amino acid derivative of claim 1, which is in the form of an acid addition salt.

7. An antihypertensive pharmaceutical composition comprising an effective amount of one or more of the amino acid derivatives of claim 1 and a pharmaceutically acceptable diluent or carrier.

8. The antihypertensive pharmaceutical composition of claim 7, wherein said composition comprises about 0.2–500 mg of said amino acid derivatives.

9. A method of treating hypertension in mammals which comprises administering to said hypertensive mammal an effective amount of the composition of claim 1.

10. The method of treating hypertension of claim 9, wherein said composition is administered in such a manner such that a total of about 1 to 2000 mg of the amino acid derivatives are administered to mammal per day.

11. The method of treating hypertension of claim 10, wherein said mammal is a human.

* * * * *

UNITED STATES PATENT AND TRADEMARK OFFICE
CERTIFICATE OF CORRECTION

PATENT NO. : 4,719,200

DATED : January 12, 1988

INVENTOR(S) : Chikahiko Eguchi et al

It is certified that error appears in the above-identified patent and that said Letters Patent is hereby corrected as shown below:

Column 1, line 24: change "snythesize", to -- synthesize --;

Column 1, line 41: change "R-or", to -- R- or --;

Column 1, line 42: after "represents", insert -- a --;

Column 1, line 43: after "$RSO_2$-", insert -- , --;

Column 1, line 47: change "OR", to -- or --;

Column 1, line 54: change "OR" to -- or --;

Column 2, line 35: change "R-or", to -- R- or --;

Column 2, line 36: change "R-or", to -- R- or --;

Column 3, line 1: delete "indo-";

Column 3, line 2: delete "lyl,";

Column 3, line 27: after "substituted", insert -- . --;

Column 4, line 3: after "reaction", insert -- . --;

Column 4, line 18: change "non-toxic", to -- nontoxic --.

Column 4, line 44: change "recomnended", to -- recommended --;

Column 6, line 37: after "pressure", insert -- . --;

Column 6, line 50: after "sure", insert -- . --;

UNITED STATES PATENT AND TRADEMARK OFFICE
CERTIFICATE OF CORRECTION

PATENT NO. : 4,719,200

DATED : January 12, 1988

INVENTOR(S) : Chikahiko Eguchi et al

It is certified that error appears in the above-identified patent and that said Letters Patent is hereby corrected as shown below Column 7, line 38: delete the entire line;

Column 7, line 44: change "(2.4 g. 6.0 m mole)", to
-- (2.4 g, 6.0 mmole) --;

Column 7, line 45: change "(1.34 g, 13.2 m mole)" to
-- (1.34 g, 13.2 mmole) --;

Column 7, line 47: change "(0.85 g 6.6 m mole)", to
-- (0.85 g, 6.6 mmole) --;

Column 7, line 64: change "methanolether", to
-- methanol:ether --;

Column 8, line 9: change "(2.05 g. 5 m mole)", to
-- (2.05 g, 5 mmole) --;

Column 8, line 14: change "(0.96 g. 5 m mole)", to
-- (0.96 g, 5 mmole) --;

Column 8, line 20: after "order", insert -- . --;

Column 8, line 26: change "benzylester" to -- benzyl ester --;

Column 8, line 46: change "(2.83 g. 10 m mole)", to
-- (2.83 g, 10 mmole) --;

UNITED STATES PATENT AND TRADEMARK OFFICE
CERTIFICATE OF CORRECTION

PATENT NO. : 4,719,200

DATED : January 12, 1988

INVENTOR(S) : Chikahiko Eguchi et al

It is certified that error appears in the above-identified patent and that said Letters Patent is hereby corrected as shown below:

Column 8, line 49: change "(1.47 g. 10 m mole)", to
-- (1.47 g, 10 mmole);

Column 8, line 58: change "extrated", to -- extracted --;

Column 8, line 65: change "acetate carbon", to
-- acetate:carbon --.

Column 9, line 14: change "dioxance", to -- dioxane --;

Column 9, line 26: change "(1.48 g)" to -- (1.46 g.) --;

Column 9, line 31: change "(br,1H),", to -- (br, 1H). --;

Column 9, line 37: change "L prolyl-", to -- L-prolyl- --;

Column 9, line 38: change "L-alanyl-1-" to -- L-alanyl-L- --;

Column 9, line 38: change "(2.83 g. 10 m mole)", to
-- (2.83 g, 10 mmole) --;

Column 9, line 51: after "residue", insert -- . --;

Column 10, line 11: change "pH2", to -- pH 2 --;

Column 10, line 42: after "was", insert -- dissolved in --;

Column 11, line 40: change "N-benzyl sulfonyl", to
-- N-benzylsulfonyl --;

UNITED STATES PATENT AND TRADEMARK OFFICE
CERTIFICATE OF CORRECTION

PATENT NO. : 4,719,200

DATED : January 12, 1988

INVENTOR(S) : Chikahiko Eguchi et al

It is certified that error appears in the above-identified patent and that said Letters Patent is hereby corrected as shown below:

Column 11, line 43: change "q,", to -- g, --;

Column 11, line 50: change "L-alanyl-L", to -- L-alanyl-L- --;

Column 12, line 5: change "L-alanyl-Lprolyl-", to
-- L-alanyl-L-prolyl- --;

Column 12, line 34: change "(21,2 ml, 21.2 m mole)", to
-- (21.2 ml, 21.2 mmole) --;

Column 12, line 35: change "(1,49 g, 10.6 m mole)", to
-- (1.49 g, 10.6 mmole) --;

Column 13, line 17: begin a new paragraph at "NMR ...";

Column 13, line 21: change "(s, 1H),", to -- (s, 1H). --;

Column 13, line 28: change " ... L-alanly-L", to
-- ... L-alanyl-L;

Column 13, line 45: change "5 74 ppm", to -- 5.74 ppm --;

Column 13, line 50: change "sepctrum", to -- spectrum --;

Column 13, line 52: change "line-L-arginine salt", to
-- line L-arginine salt --;

Column 13, line 54: change (0.41" to, -- (0.418 -- ;

UNITED STATES PATENT AND TRADEMARK OFFICE
CERTIFICATE OF CORRECTION

PATENT NO. : 4,719,200

DATED : January 12, 1988

INVENTOR(S) : Chikahiko Eguchi et al

It is certified that error appears in the above-identified patent and that said Letters Patent is hereby corrected as shown below:

Column 13, line 55: delete "8";

Column 14, line 4: change "standard TMS:", to -- standard:TMS --;

Column 14, line 34: change "sufate", to -- sulfate --;

Column 14, line 49: change "(1.00 g-2.49 m mole)", to -- (1.00 g, 2.49 mmole) --;

Column 15, line 22: change "benzyloxcarbonyl-", to -- benzyloxycarbonyl --;

Column 15, line 26: change "ml", to -- ml) --;

Column 15, line 44: change "$C_{18}H_{28}N_4O_5 \cdot CH_3OH \cdot H_2O.$", to -- $C_{18}H_{28}N_4O_5 \cdot CH_3OH \cdot H_2O.$ --;

Column 16, line 32: change "ml,", (1st occurance) to --ml)--;

Column 16, line 52: after "gas", insert -- was --;

Column 16, line 60: change "$C_{18}H_{25}N_4O_6 \cdot CH_3OH \cdot 0.75H_2O.$", to -- $C_{18}H_{25}N_4O_6 \cdot CH_3OH \cdot 0.75 H_2O.$ --;

Column 17, line 12: change "bean", to -- been --;

UNITED STATES PATENT AND TRADEMARK OFFICE
CERTIFICATE OF CORRECTION

PATENT NO. : 4,719,200

DATED : January 12 1988

INVENTOR(S) : Chikahiko Eguchi et al

It is certified that error appears in the above-identified patent and that said Letters Patent is hereby corrected as shown below:

Column 17, line 27:   change "methanolether", to --methanol:ether--;

Column 18, line 1:   change "mode)", to --mode]--;

Column 18, line 12:   change "exchnge", to --exchange--;

Column 18, line 16:   change "(d.", to --(d,--;

Table I, Example 27:   under "starting materials", change "prolinebenzyl-" to --proline benzyl--;

Table I, Example 30:   same heading, change "carbonylchloride", to --carbonyl chloride--;

Table I, Example 33:   same heading, change "ethoxycarboxyl", to --ethoxycarbonyl--;

Table I, Example 35:   same heading, change "ethoxycarboxylchloride", to --ethoxycarbonyl chloride--;

Table I, Example 36:   under heading "Product", change "methionyl-L-prolyl-L", to --methionyl-L-prolyl-L- --;

UNITED STATES PATENT AND TRADEMARK OFFICE
CERTIFICATE OF CORRECTION

PATENT NO. : 4,719,200
DATED : January 12, 1988
INVENTOR(S) : Chikahiko Eguchi et al It is certified that error appears in the above-identified patent and that said Letters Patent is hereby corrected as shown below:

Table I, Example 37: under heading "Starting Materials", change "ethan-", to -- ethane- --;

Table I, Example 40: under heading "Product", change "ethane sulfonyl", to -- ethanesulfonyl --, and "L proline", to -- L-proline --;

Table I, Example 40: under heading "Starting Materials", change "benzylester", to -- benzyl ester --, and "ethansulfonyl", to -- ethanesulfonyl --;

Table I, Example 41: under heading "Product", change "ethane sulfonyl" to -- ethanesulfonyl --;

Table I, Example 42: under heading "Product", change "ethane sulfonyl" to -- ethanesulfonyl --;

Table I, Example 42: under heading "Starting Materials", after "chloride", insert -- , --;

Table I, Example 42: under heading "TLC, Rf Value", change "945", to -- 0.45 --;

UNITED STATES PATENT AND TRADEMARK OFFICE
CERTIFICATE OF CORRECTION

PATENT NO. : 4,719,200

DATED : January 12, 1988

INVENTOR(S) : Chikahiko Eguchi et al

It is certified that error appears in the above-identified patent and that said Letters Patent is hereby corrected as shown below:

Table I, Example 43: under heading "Product", change "ethane sulfonyl" to -- ethanesulfonyl --;

Column 21, Example 29, second line: change "(,m2H)," to -- (m,2H) --;

Column 21, Example 33, third line: change "(d.1H)" to -- (d,1H) --;

Column 21, Example 38, third line: change "(m5H)" to -- (m, 5H) --;

Column 22, Example 42, second line: delete "w";

Column 23, line 21: change "R40", to -- R' --;

UNITED STATES PATENT AND TRADEMARK OFFICE
CERTIFICATE OF CORRECTION

PATENT NO. : 4,719,200

DATED : January 12, 1988

INVENTOR(S) : Chikahiko Eguchi et al

It is certified that error appears in the above-identified patent and that said Letters Patent is hereby corrected as shown below:

Column 24, line 28: change "are", to --is--;

and after "to", insert --a--.

Signed and Sealed this

Seventeenth Day of March, 1992

Attest:

HARRY F. MANBECK, JR.

*Attesting Officer*      *Commissioner of Patents and Trademarks*